(12) United States Patent
Sugahara

(10) Patent No.: US 11,937,965 B2
(45) Date of Patent: Mar. 26, 2024

(54) RADIOGRAPHIC SYSTEM

(71) Applicant: FUJIFILM Corporation, Tokyo (JP)

(72) Inventor: Masataka Sugahara, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 305 days.

(21) Appl. No.: 17/496,769

(22) Filed: Oct. 8, 2021

(65) Prior Publication Data

US 2022/0022835 A1 Jan. 27, 2022

Related U.S. Application Data

(63) Continuation of application No. PCT/JP2020/015838, filed on Apr. 8, 2020.

(30) Foreign Application Priority Data

Apr. 11, 2019 (JP) .................................. 2019-075863
Nov. 12, 2019 (JP) .................................. 2019-204754

(51) Int. Cl.
*A61B 6/10* (2006.01)
*A61B 6/00* (2006.01)
*A61B 6/08* (2006.01)

(52) U.S. Cl.
CPC .................. *A61B 6/54* (2013.01); *A61B 6/08* (2013.01); *A61B 6/464* (2013.01)

(58) Field of Classification Search
CPC .... A61B 1/00; A61B 1/04; A61B 1/06; A61B 1/0605; A61B 6/04; A61B 6/461; A61B 6/467; A61B 2576/00
See application file for complete search history.

(56) References Cited

U.S. PATENT DOCUMENTS

| | | | |
|---|---|---|---|
| 10,842,457 | B2 | 11/2020 | Tajima |
| 2013/0121556 | A1 | 5/2013 | Matsumoto |
| 2016/0287194 | A1 | 10/2016 | Nariyuki et al. |
| 2017/0196525 | A1 | 7/2017 | Kim et al. |
| 2017/0360390 | A1 | 12/2017 | Tajima |

(Continued)

FOREIGN PATENT DOCUMENTS

| | | |
|---|---|---|
| JP | 2011045709 | 3/2011 |
| JP | 2011255061 | 12/2011 |
| JP | 2012010772 | 1/2012 |

(Continued)

OTHER PUBLICATIONS

"Notice of Reasons for Refusal of Japan Counterpart Application", dated Sep. 13, 2022, with English translation thereof, p. 1-p. 12.

(Continued)

*Primary Examiner* — Don K Wong
(74) *Attorney, Agent, or Firm* — JCIPRNET

(57) ABSTRACT

The radiographic system includes a camera that images a subject, a processor, and a display, in which the processor recognizes whether or not arrangement of the subject in a camera image captured using the camera matches arrangement of the subject in the imaging menu, and displays a first display mode for indicating presence of a result of the recognition, and displays a second display mode for displaying a content of the recognition result in a case of receiving an explicit display request for the recognition result, on the display.

12 Claims, 10 Drawing Sheets

(56) References Cited

U.S. PATENT DOCUMENTS

2018/0192970 A1* 7/2018 Tajima .................. A61B 6/461
2019/0046130 A1   2/2019 Imamura et al.

FOREIGN PATENT DOCUMENTS

| JP | 2013102851 | 5/2013 |
| JP | 2016097225 | 5/2016 |
| WO | 2016136415 | 9/2016 |

OTHER PUBLICATIONS

"Search Report of Europe Counterpart Application", dated May 3, 2022, p. 1-p. 7.

"International Search Report (Form PCT/ISA/210) of PCT/JP2020/015838," dated Jun. 30, 2020, with English translation thereof, pp. 1-5.

"Written Opinion of the International Searching Authority (Form PCT/ISA/237)" of PCT/JP2020/015838, dated Jun. 30, 2020, with English translation thereof, pp. 1-6.

"Office Action of China Counterpart Application", dated Nov. 13, 2023, with English translation thereof, pp. 1-15.

* cited by examiner

RADIOGRAPHIC SYSTEM

CROSS-REFERENCE TO RELATED APPLICATIONS

This application is a Continuation of PCT International Application No. PCT/JP2020/015838 filed on 8 Apr. 2020, which claims priority under 35 U.S.C § 119(a) to Japanese Patent Applications No. 2019-075863 filed on 11 Apr. 2019 and No. 2019-204754 filed on 12 Nov. 2019. The above application is hereby expressly incorporated by reference, in its entirety, into the present application.

BACKGROUND

1. Technical Field

The present disclosure relates to a radiographic system that images a subject using radiation.

2. Description of the Related Art

In the related art, a radiographic apparatus that images a subject by using radiation such as X-rays has become widespread. For example, in a case where the subject is a person or an animal, a radiation image is used for diagnosis of a lesion or the like.

The radiographic apparatus includes, for example, a radiation source that generates radiation, a radiographic panel that images the subject by using radiation transmitted through the subject, and a console as a control table that sets an imaging menu. The imaging menu is a menu relating to radiography in which imaging conditions and the like are set based on a request for radiography (imaging order) received from a doctor or the like.

In recent years, there has been known an X-ray image diagnostic apparatus that determines a part of a subject using a camera image obtained by imaging an X-ray irradiation region with a camera, and permits X-ray irradiation only in a case where the determined part matches a imaging condition (JP2016-097225A). In addition, there has been known a radiography apparatus that determines, in a case where radiography on a breast of a subject being tested is performed, whether an imaging part is the right breast or the left breast according to an orientation of a face of the subject being tested, and provides notification to an operator in a case where the left and right of the determined imaging part and the left and right of an imaging part set in an imaging menu do not match each other (JP2012-010772A).

SUMMARY

Radiography needs to be performed appropriately in accordance with an imaging menu set or selected. This is to provide an appropriate radiation image according to an imaging order for diagnosis and the like.

However, in a case where radiography is performed actually, radiography may be performed in a manner that an orientation of a subject does not match the imaging menu. In this case, since the obtained radiation image does not correspond to an imaging order, it may not be possible to perform an appropriate diagnosis or the like. For example, in a case where a radiation image obtained by posterior-anterior (PA) view imaging is provided to an imaging order for anterior-posterior (AP) view imaging of the chest of a specific subject being tested who is a subject, the misidentification of the left and right of a disease position and/or the misidentification of situs inversus may be caused in diagnosis.

Therefore, a radiographic system may support imaging by determining whether or not an imaging part is correct, but there is a case where a radiological technician, a doctor, or the like (hereinafter, referred to as a radiological technician or the like) may rely too much on the support from the radiographic system. For example, although a result of the determination for supporting the imaging has a certain degree of accuracy, a possibility of outputting a recognition result with a low accuracy cannot be completely excluded in a specific situation in reality. However, a radiological technician or the like may implicitly exclude a possibility that there is an error in the result of the determination. In a case where such excessive reliance occurs, there is a case where imaging in accordance with an imaging menu cannot be performed as a result of the support of the radiographic system.

The present disclosure provides a radiographic system capable of preventing excessive reliance by a radiological technician or the like and appropriately supporting radiography in accordance with an imaging menu.

A radiographic system according to an aspect of the present disclosure comprises a radiation source, a radiographic unit, a camera, a processor, and a display. The radiation source generates radiation. The radiographic unit images a subject using the radiation. The camera images the subject arranged with respect to the radiographic unit. The processor sets an imaging menu, recognizes whether or not arrangement of the subject in a camera image captured using the camera matches arrangement of the subject in the imaging menu, and displays a first display mode for indicating presence of a result of the recognition, and displays a second display mode for displaying a content of the recognition result in a case of receiving an explicit display request for the recognition result, on the display.

It is preferable that the display is located in a blind spot of the radiographic unit.

It is preferable that the display is provided in the radiation source.

It is preferable that the display is a tablet terminal.

It is preferable that a plurality of the displays are provided.

It is preferable that the plurality of displays have different display aspects of the recognition result, respectively.

It is preferable that the processor recognizes whether or not an orientation of the subject in the camera image matches an orientation of the subject in the imaging menu.

It is preferable that the processor recognizes an orientation of the subject whose back faces the radiation source and an orientation of the subject whose abdomen faces the radiation source.

It is preferable that the processor recognizes whether or not an imaging part of the subject recognized by using the camera image matches an imaging part of the subject in the imaging menu.

It is preferable that the processor displays, on the display, a warning indicating that the arrangement of the subject in the camera image does not match the arrangement of the subject in the imaging menu.

It is preferable that the processor displays, on the display, arrangement support information for supporting the arrangement of the subject in the camera image to match the arrangement of the subject in the imaging menu.

It is preferable that the processor prohibits irradiation with the radiation in a case where the arrangement of the subject in the camera image does not match the arrangement of the subject in the imaging menu.

The radiographic system according to the aspect of the present disclosure can prevent excessive reliance by a radiological technician or the like, and can appropriately support radiography in accordance with an imaging menu.

DESCRIPTION OF THE PREFERRED EMBODIMENTS

Figure 1:
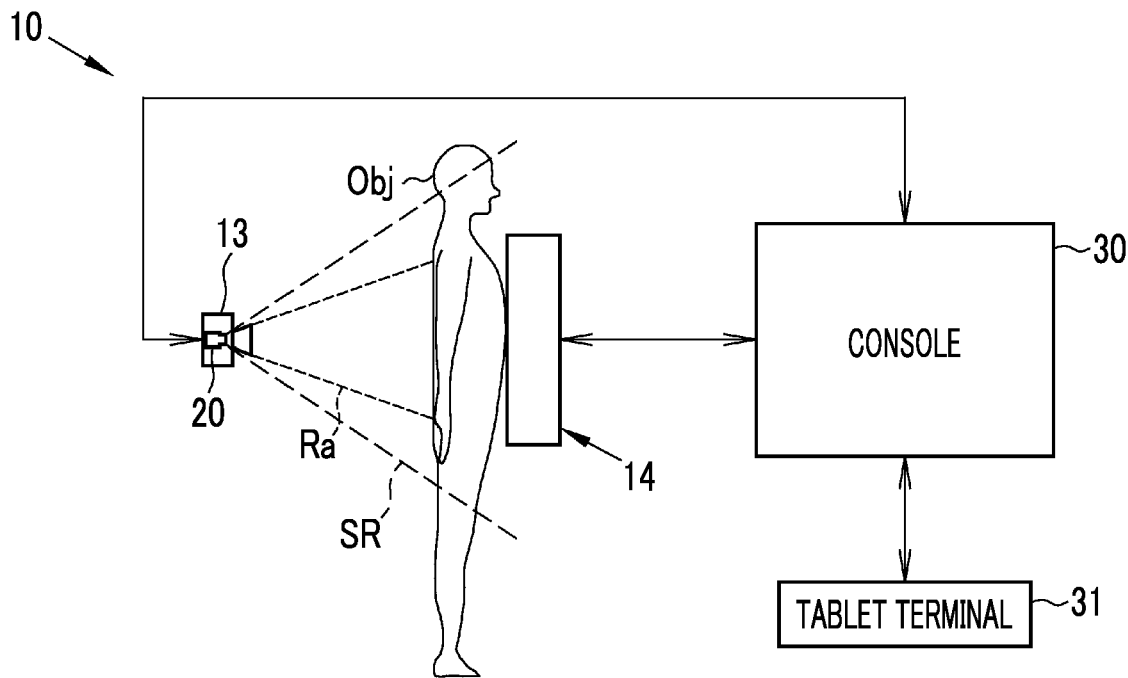
FIG. 1 is an explanatory diagram showing a configuration of a radiographic system.

As shown in FIG. 1, a radiographic system 10 comprises a radiation source 13, a radiographic unit 14, a camera 20, a console 30, and a tablet terminal 31. The radiation source 13, the radiographic unit 14, and the console 30 constitute a radiographic apparatus.

Figure 2:
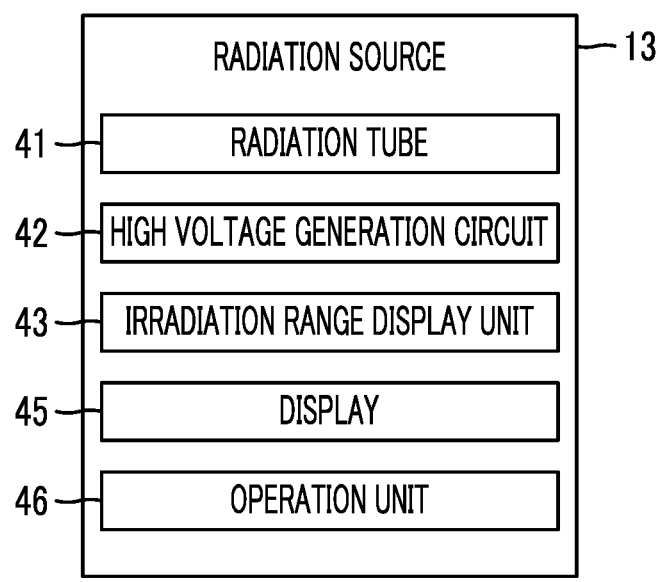
FIG. 2 is a block diagram of a radiation source.

The radiation source 13 generates radiation Ra used for radiography. Therefore, as shown in FIG. 2, the radiation source 13 includes a radiation tube 41 that generates the radiation Ra, a high voltage generation circuit 42 that generates a high voltage required for the radiation tube to generate the radiation Ra, and the like. The radiation source 13 can generate a plurality of types of radiation having different radiation qualities (that is, energy distribution) by adjusting the tube voltage and the tube current of the radiation tube 41. The energy of the radiation Ra generated by the radiation source 13 is one of imaging conditions. In the present embodiment, the radiation source 13 is an X-ray source that generates X-rays. Therefore, the radiographic system 10 is an X-ray imaging system that acquires an X-ray image of a subject Obj by imaging the subject Obj using X-rays. The subject Obj is, for example, a person.

In addition, in the present embodiment, the radiation source 13 comprises an irradiation range display unit 43, a display 45, and an operation unit 46. The irradiation range display unit 43 projects an image representing an irradiation position and/or range (it is a so-called irradiation range or irradiation field; hereinafter, referred to as an irradiation range) of the radiation Ra onto the subject Obj or the like. Thus, the irradiation range display unit 43 displays the irradiation range of the radiation Ra.

The display 45 is a display that displays an imaging menu or the like in the radiation source 13, and is separate from the console 30. As will be described below, in the present embodiment, the display 45 displays the presence of a recognition result by a recognition unit 54 (see FIG. 3) and the content of the recognition result in a case where at least the arrangement of the subject Obj in a camera image does not match the arrangement of the subject Obj in the imaging menu. In addition, the display 45 displays a first display mode for indicating the presence of the recognition result (see FIG. 10), and displays a second display mode for displaying the content of the recognition result in a case where an explicit display request for the recognition result is received (see FIG. 11). Regarding the display request, the term "explicit" means that there is an input such as operation or setting to the radiographic system 10 based on the intention or determination of a radiological technician or the like.

The operation unit 46 is a physical button or switch, a graphical user interface (GUI), or the like, and the operation unit 46 can be used, for example, to perform on/off switching of the irradiation range of the radiation Ra, or to set the tube voltage of the radiation tube 41. In addition, the operation unit 46 can be used to input a "display request for recognition result" that explicitly requests the display of the content of the recognition result. The display 45 and the operation unit 46 can be integrated and constituted by a touch panel.

The radiographic unit 14 images the subject Obj using the radiation Ra generated by the radiation source 13. The radiographic unit 14 includes a so-called radiation detector, and is, for example, a flat panel detector (FPD). The FPD outputs a radiation image of the subject Obj by detecting the radiation Ra transmitted through the subject Obj and converting it into an electric signal. In the imaging using the radiographic unit 14, a grid (not shown) can be used in combination as needed. The grid is a device that removes scattered radiation components of radiation, for example, a static type Lysholm blende, a mobile type Bucky blende, or the like. In the present embodiment, the radiographic unit 14 includes one radiation detector and outputs one radiation image by one time of irradiation of the radiation Ra, but the radiographic unit 14 may include a plurality of radiation detectors. In a case where the radiographic unit 14 includes a plurality of radiation detectors, the radiographic unit 14 can output a plurality of radiation images by one time of irradiation of the radiation Ra.

The radiation detector included in the radiographic unit 14 may be either an indirect conversion type radiation detector or a direct conversion type radiation detector. In a case where the radiographic unit 14 includes a plurality of radiation detectors, a plurality of different types of radiation detectors can be used in combination. The indirect conversion type radiation detector is a detector that indirectly obtains an electric signal by converting the radiation Ra into visible light using a scintillator made of cesium iodide (CsI) or the like and photoelectrically converting the visible light. The direct conversion type radiation detector is a detector that directly converts the radiation Ra into an electric signal using a scintillator made of amorphous selenium or the like. In addition, the radiation detector included in the radiographic unit 14 may be a penetration side sampling (PSS) method radiation detector or an irradiation side sampling (ISS) method radiation detector. The PSS method is a method in which a scintillator is arranged on the subject Obj side with respect to a thin film transistor (TFT) that reads out an electric signal. Contrary to the PSS method, the ISS method is a method in which the scintillator and the TFT are arranged in the order of the TFT and the scintillator from the subject Obj side.

The camera 20 images the subject Obj arranged with respect to the radiographic unit 14 by using visible light, infrared light, or the like (light having a wavelength or energy distribution different from that of the radiation Ra). More specifically, the camera 20 is, for example, a digital camera or a digital video camera. In addition, an imaging range SR of the camera 20 includes at least an irradiation range of the radiation Ra. In the radiographic system 10, an image (including a motion picture as a collection of still images; hereinafter, referred to as a camera image) captured using the camera 20 is used for recognition of arrangement of the subject Obj in radiography. Therefore, the camera image includes at least a part or the whole of the irradiation range of the radiation Ra to the extent that the recognition process can be performed. In the present embodiment, the camera 20 is a digital video camera, and the subject Obj is imaged using visible light. Although the camera 20 is randomly arranged within a range in which the subject Obj can be imaged in the irradiation range of the radiation Ra, in the present embodiment, the camera 20 is provided substantially integrally with the radiation source 13. This is to surely image the subject Obj arranged in the irradiation range of the radiation Ra without excess or deficiency to the extent that the above recognition process can be performed.

Figure 3:
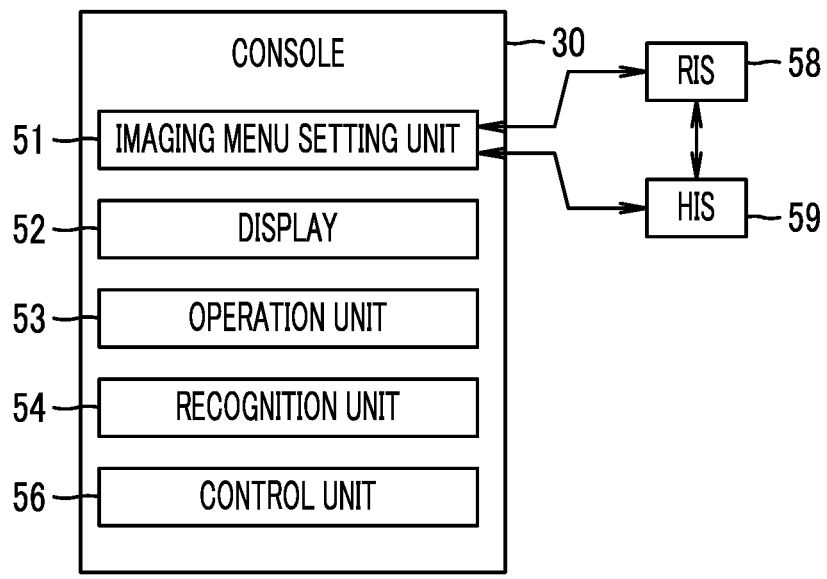
FIG. 3 is a block diagram of a console.

The console 30 is a main control device (so-called computer) of the radiographic system 10, comprises a processor, and sets, for example, an imaging menu. As shown in FIG. 3, the console 30 comprises an imaging menu setting unit 51, a display 52, an operation unit 53, a recognition unit 54, and a control unit 56. In the console 30, programs relating to processes of the imaging menu setting unit 51, the display 52, the operation unit 53, the recognition unit 54, and the control unit 56 are incorporated in a memory (not shown). The programs are operated by a central control unit (not shown) composed of a processor, whereby functions of the imaging menu setting unit 51, the display 52, the operation unit 53, the recognition unit 54, and the control unit 56 are realized.

The imaging menu setting unit 51 acquires an imaging order by manual input or from radiology information systems (RIS) 58, hospital information systems (HIS) 59, or other external system. Then, an imaging menu is set according to the acquired imaging order. The imaging order is a request for radiography, and includes, for example, information (identification number of a subject being tested who is the subject Obj) for specifying the subject Obj and information for specifying the imaging part and imaging direction of the subject Obj. The imaging menu is a menu showing specific imaging items, and is set according to the imaging order. For example, in a case where the imaging order is "imaging request for each one of chest front (P→A) and chest front (A→P) of the specific subject Obj", the imaging menu setting unit 51 sets "chest front (P→A)" and "chest front (A→P)" as the imaging menu for the specific subject Obj. The term "chest front (P→A)" means a menu in which the radiation Ra is emitted from the rear surface (posterior) toward the front surface (anterior) of the subject Obj to image the chest of the subject Obj from the front. In addition, the term "chest front (A→P)" means a menu in which the radiation Ra is emitted from the front surface toward the rear surface of the subject Obj to image the chest of the subject Obj from the front.

The display 52 is, for example, a liquid crystal display, and displays a captured radiation image and other necessary operations or settings. For example, the display 52 displays the presence of the recognition result by the recognition unit 54 and the content of the recognition result in a case where at least the arrangement of the subject Obj in a camera image does not match the arrangement of the subject Obj in the imaging menu. In addition, the display 52 displays a first display mode for indicating the presence of the recognition result (see FIG. 8), and displays a second display mode for displaying the content of the recognition result in a case where an explicit display request for the recognition result is received (see FIG. 9).

The operation unit 53 is, for example, a keyboard and/or a pointing device used for setting input of the imaging conditions and the like and for operating the radiation source 13 and the radiographic unit 14. In addition, the operation unit 53 can be used to input a "display request for recognition result" that explicitly requests the display of the content of the recognition result. The display 52 and the operation unit 53 can be constituted by a touch panel.

The recognition unit 54 recognizes whether or not the arrangement of the subject Obj in the camera image captured using the camera 20 matches the arrangement of the subject Obj in the imaging menu. The arrangement of the subject Obj in the camera image is the arrangement of the subject Obj recognized by using the camera image. The arrangement of the subject Obj in the imaging menu is the arrangement of the subject Obj designated by the imaging menu. For example, in a case where the imaging menu is "chest front (P→A)", "P→A" is the arrangement of the subject Obj. That is, an orientation of the subject Obj whose rear surface (back side surface) faces the radiation source 13 and whose front surface (abdominal side surface) faces the radiographic unit 14 is the arrangement of the subject Obj in the imaging menu of "chest front (P→A)".

The imaging range in radiography is determined by a relative positional relationship between the radiation source 13 and the radiographic unit 14. Specifically, an overlapping portion of the irradiation range (range in which effective pixels contributing to the radiation image are arranged) of the radiation Ra and the effective imaging range of the radiographic unit 14 is the imaging range in radiography. The arrangement (positioning) of the subject Obj means the position and/or orientation of the subject Obj in the "imaging range". The portion of the subject Obj in the imaging range is the imaging part of the subject Obj. The orientation of the subject Obj in the imaging range is the direction in which the imaging part is captured (imaging direction) and the direction in which the radiation Ra is emitted to the imaging part. In the present embodiment, the recognition unit 54 recognizes whether or not at least the orientation of the subject Obj in the camera image matches the orientation of the subject Obj in the imaging menu.

The recognition of the subject Obj in the camera image can be performed using characteristics relating to a shape of the whole or part of the subject Obj. For example, in a case where the subject Obj is a person and the camera image includes the face of the subject Obj, the subject Obj can be recognized in the camera image by determining the position and orientation of the face of the subject Obj. In addition, the recognition unit 54 can be realized by an artificial intelligence (AI) program that has been learned by machine learning or the like.

The control unit 56 comprehensively controls the operation of the radiographic system 10. For example, the control unit 56 prohibits irradiation with the radiation Ra in a case where the arrangement of the subject Obj in the camera image does not match the arrangement of the subject Obj in the imaging menu. As a result, the execution of radiography is prohibited. This is to prevent the execution of radiography with a mistake (positioning mistake) in the arrangement of the subject Obj and surely, and as a result, to prevent misidentification of a disease position or the like in diagnosis. The term "prohibit" for irradiation with the radiation Ra means no irradiation with the radiation Ra regardless of the instruction input from a radiological technician or the like, and includes no irradiation with the radiation Ra as a result of not receiving the instruction input relating to irradiation with the radiation Ra, not generating the radiation Ra, and not executing preliminary operation for generating the radiation Ra. For example, the control unit 56 prohibits the irradiation with the radiation Ra by inactivating a GUI switch, locking a mechanical switch, or the like.

The control unit 56 controls the display contents and display aspects of the display 45 of the radiation source 13, the display 52 of the console 30, and a display 61 (see FIG. 4) of the tablet terminal 31. For example, a display that is at least separate from the console 30, that is, the display 45 of the radiation source 13 and the display 61 of the tablet terminal 31 displays the presence of the recognition result by the recognition unit 54 (or the content of the recognition result) in a case where at least the arrangement of the subject Obj in the camera image does not match the arrangement of the subject Obj in the imaging menu. In the present embodiment, in a case where the arrangement of the subject Obj in the camera image does not match the arrangement of the subject Obj in the imaging menu, the control unit 56 displays a first display mode for displaying the presence of the recognition result on the display 45 of the radiation source 13, the display 52 of the console 30, and the display 61 of the tablet terminal 31.

In a case where the control unit 56 receives the "display request for recognition result" input by using the operation unit 46 of the radiation source 13, the control unit 56 switches the display aspect of the display 45 of the radiation source 13 from the first display mode to the second display mode. That is, the control unit 56 displays the content of the recognition result on the display 45 of the radiation source 13 by receiving the "display request for recognition result" using the operation unit 46 of the radiation source 13. In addition, in a case where the control unit 56 receives the "display request for recognition result" input by using the operation unit 53 of the console 30, the control unit 56 switches the display aspect of the display 52 of the console 30 from the first display mode to the second display mode. That is, the control unit 56 displays the content of the recognition result on the display 52 of the console 30 by receiving the "display request for recognition result" using the operation unit 53 of the console 30. Similarly, in a case where the control unit 56 receives the "display request for recognition result" input by using an operation unit 62 of the tablet terminal 31, the control unit 56 switches the display aspect of the display 61 of the tablet terminal 31 from the first display mode to the second display mode. That is, the control unit 56 displays the content of the recognition result on the display 61 of the tablet terminal 31 by receiving the "display request for recognition result" using the operation unit 62 of the tablet terminal 31.

The tablet terminal 31 is a sub-control device of the radiographic system 10. The tablet terminal 31 is portable and can perform some or all of the settings, controls, and/or displays performed using the console 30 or the operation unit 46 of the radiation source 13. Therefore, the tablet terminal 31 can be used on the spot in a case of adjusting the arrangement of the subject Obj, such as in the vicinity of the radiation source 13 and/or the radiographic unit 14.

Figure 4:
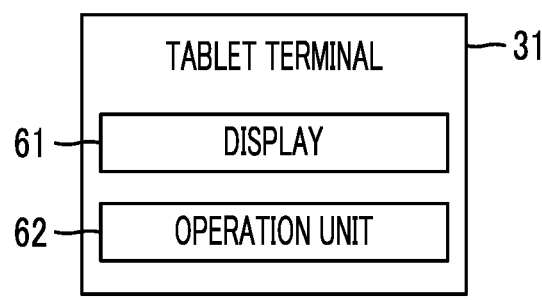
FIG. 4 is a block diagram of a tablet terminal.

As shown in FIG. 4, the tablet terminal 31 comprises the display 61 and the operation unit 62, and communicates with the radiation source 13, the radiographic unit 14, and/or the console 30 as needed. The display 61 is separate from the console 30, and displays a camera image, a radiation image, other images (including a motion picture), and/or a setting screen or a control screen (GUI or the like) using the radiographic system 10 for control. In addition, the display 61 displays the presence of the recognition result by the recognition unit 54 or the content of the recognition result in a case where at least the arrangement of the subject Obj in a camera image does not match the arrangement of the subject Obj in the imaging menu. In addition, the display 61 displays a first display mode for indicating the presence of the recognition result (see FIG. 12), and displays a second display mode for displaying the content of the recognition result in a case where an explicit display request for the recognition result is received (see FIG. 13).

The operation unit 62 is an input device used for setting input of the imaging conditions and the like and for operating the radiation source 13 and the radiographic unit 14. In addition, the operation unit 62 can be used to input the "display request for recognition result" that explicitly requests the display of the content of the recognition result. The display 61 and the operation unit 62 can be constituted by using, for example, a touch panel.

Figure 5:
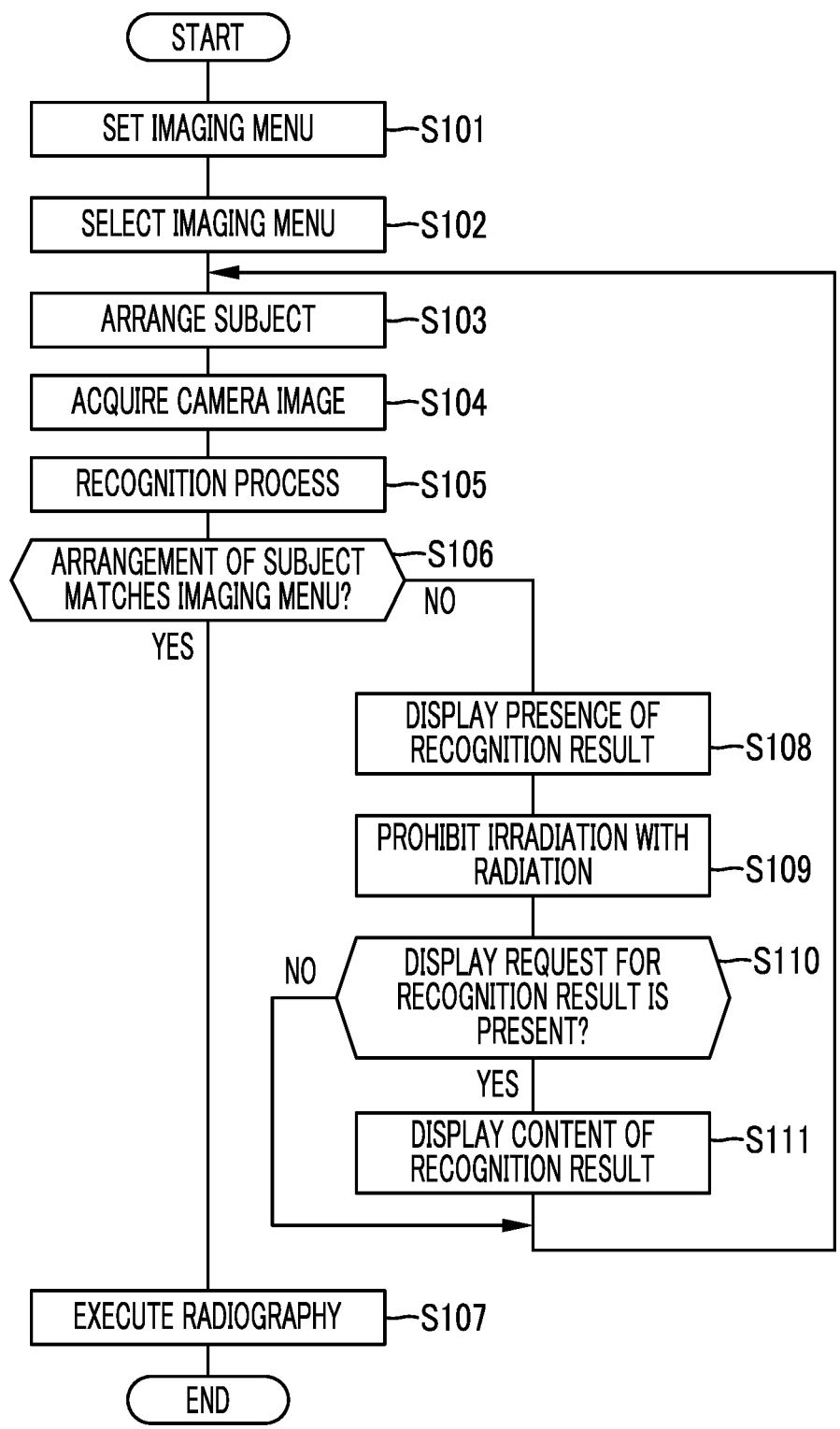
FIG. 5 is a flowchart of radiography.

A flow of radiography using the radiographic system 10 constituted as described above will be described. As shown in FIG. 5, the imaging menu setting unit 51 acquires an imaging order automatically or by manual input, and sets an imaging menu according to the acquired imaging order (step S101). The imaging menu set by the imaging menu setting unit 51 is displayed, for example, on the display 52 of the console 30 (see FIG. 6 and the like). Therefore, a radiological technician or the like selects an imaging menu to be executed next by using the operation unit 53 of the console 30 (step S102). After that, the radiological technician or the like arranges the subject Obj in accordance with the selected imaging menu (step S103). The selection of the imaging menu and the arrangement of the subject Obj are preparatory work for executing the imaging performed by the radiological technician or the like. The work of "arranging the subject Obj" performed by the radiological technician or the like includes selection, position, or orientation adjustment of the radiation source 13 and/or the radiographic unit 14.

On the other hand, in parallel with the work of arranging the subject Obj, the radiographic system 10 acquires a camera image by imaging the subject Obj arranged with respect to the radiographic unit 14 by the camera 20 (step S104). Thus, the recognition unit 54 can obtain information on the selected imaging menu (imaging menu to be executed) and a camera image in which the subject Obj is captured. Therefore, the recognition unit 54 recognizes whether or not the arrangement of the subject Obj in the camera image captured using the camera 20 matches the arrangement of the subject Obj in the imaging menu (step S105).

In a case where the arrangement of the subject Obj in the camera image matches the arrangement of the subject Obj in the imaging menu (step S106: YES), the radiological technician or the like inputs an instruction to execute imaging, whereby the radiographic system 10 executes radiography (step S107). On the other hand, in a case where the arrangement of the subject Obj in the camera image does not match the arrangement of the subject Obj in the imaging menu (step S106: NO), the control unit 56 displays the recognition result of the recognition unit 54 on the display 45 of the radiation source 13, the display 52 of the console 30, and the display 61 of the tablet terminal 31 in the display aspect of the first display mode for indicating the presence of the recognition result (step S108), and the control unit 56 prohibits irradiation with the radiation Ra (step S109).

Here, in a case where the radiological technician or the like inputs display request for the recognition result by using the operation unit 46 of the radiation source 13, the operation unit 53 of the console 30, and/or the operation unit 62 of the tablet terminal 31 (step S110: YES), the control unit 56 switches the display aspect of the display 45 of the radiation source 13, the display 52 of the console 30, and/or the display 62 of the tablet terminal 31 from the display of the first display mode to the display of the second display mode according to the operation unit that has input the display request for the recognition result. Thus, the display 45 of the radiation source 13, the display 52 of the console 30, and/or the display 62 of the tablet terminal 31 displays the content of the recognition result (step S111).

By viewing the display of the first display mode, the radiological technician or the like can infer that there is some defect in radiography, such as a possibility that the arrangement of the subject Obj in the camera image does not match the arrangement of the subject Obj in the imaging menu. In addition, by viewing the display of the second display mode, the radiological technician or the like can specifically know that the arrangement of the subject Obj in the camera image does not match the arrangement of the subject Obj in the imaging menu. Therefore, after viewing the display of the first display mode or the display of the second display mode, the radiological technician or the like adjusts the arrangement of the subject Obj, thereby arranging the subject Obj such that the arrangement of the subject Obj in the camera image matches the arrangement of the subject Obj in the imaging menu (step S103). Thus, radiography in accordance with the imaging menu can be correctly executed (step S107).

The display of the first display mode and the display of the second display mode on the display 52 of the console 30, the display 45 of the radiation source 13, and the display 61 of the tablet terminal 31 are performed as follows.

<Display of Console>

Figure 6:
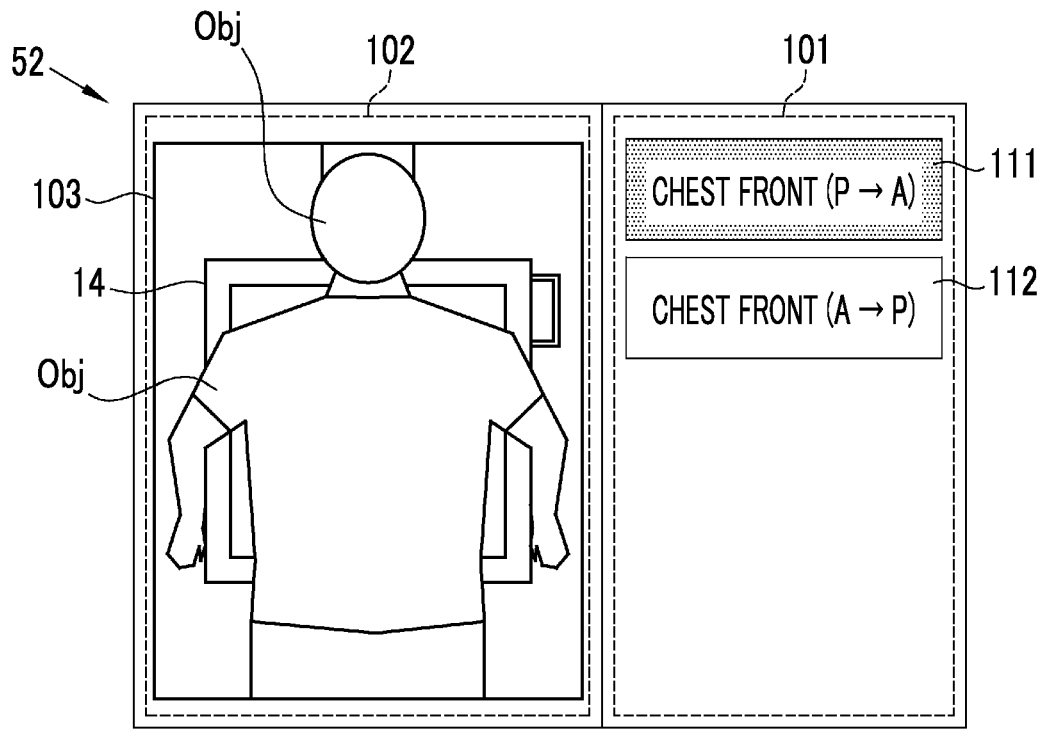
FIG. 6 is an explanatory diagram showing a display aspect of the console.

First, as shown in FIG. 6, the display 52 of the console 30 has, for example, an imaging menu display area 101 and an image display area 102. The imaging menu display area 101 displays an imaging menu set by the imaging menu setting unit 51. In a case where the imaging menu setting unit 51 sets a plurality of imaging menus based on one imaging order, the imaging menu display area 101 displays each of the plurality of imaging menus. In the present embodiment, the imaging order is "imaging request for each one of chest front (P→A) and chest front (A→P)" for a specific subject being tested (subject Obj), and the imaging menu setting unit 51 automatically sets two imaging menus from one imaging order: a first imaging menu 111 for imaging the chest of the subject Obj from the front in the rear and front (P→A) orientation; and a second imaging menu 112 for imaging the chest of the subject Obj from the front in the front and rear (A→P) orientation. Therefore, the display 52 of the console 30 displays the first imaging menu 111 and the second imaging menu 112.

As one of the imaging preparations, the radiological technician or the like uses the operation unit 53 or the like to select an imaging menu to be executed from one or a plurality of imaging menus displayed in the imaging menu display area 101. The control unit 56 displays an imaging menu in a selected state and an imaging menu in a non-selected state in the imaging menu display area 101 in such a manner that the imaging menus can be distinguished from each other. For example, FIG. 6 shows an example in which the first imaging menu 111 is in a selected state and the second imaging menu 112 is in a non-selected state. Therefore, in FIG. 6, radiography to be performed next is imaging of "chest front (P A)" of the first imaging menu 111.

The image display area 102 appropriately displays a camera image and a captured radiation image. Before the execution of radiography, the image display area 102 displays a camera image. In a camera image 103 displayed by the image display area 102 in FIG. 6, the abdomen of the subject Obj faces the radiographic unit 14 and the back of the subject Obj faces the radiation source 13 and the camera 20. That is, in the camera image 103, the subject Obj is arranged as "P→A".

Figure 7:
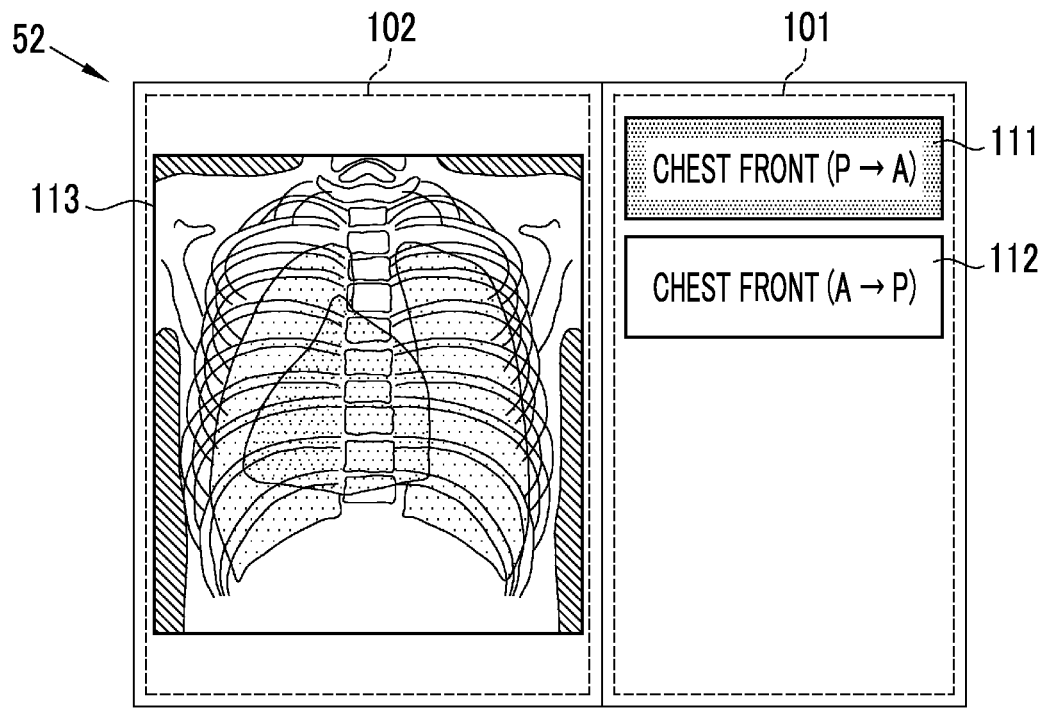
FIG. 7 is an explanatory diagram showing a display aspect of the console after radiography.

Here, since the arrangement of the subject Obj in the camera image 103 and the arrangement of the subject Obj in the first imaging menu 111 in the selected state are both "P→A" and match each other, radiography can be performed as is. Therefore, the radiological technician or the like inputs an instruction to execute imaging, whereby the radiographic system 10 executes imaging. After the execution of radiography, as shown in FIG. 7, the display 52 of the console 30 displays a captured radiation image 113 in the image display area 102. The radiation image 113 is a radiation image obtained by capturing the chest of the subject Obj from the front in the "P→A" direction.

Figure 8:
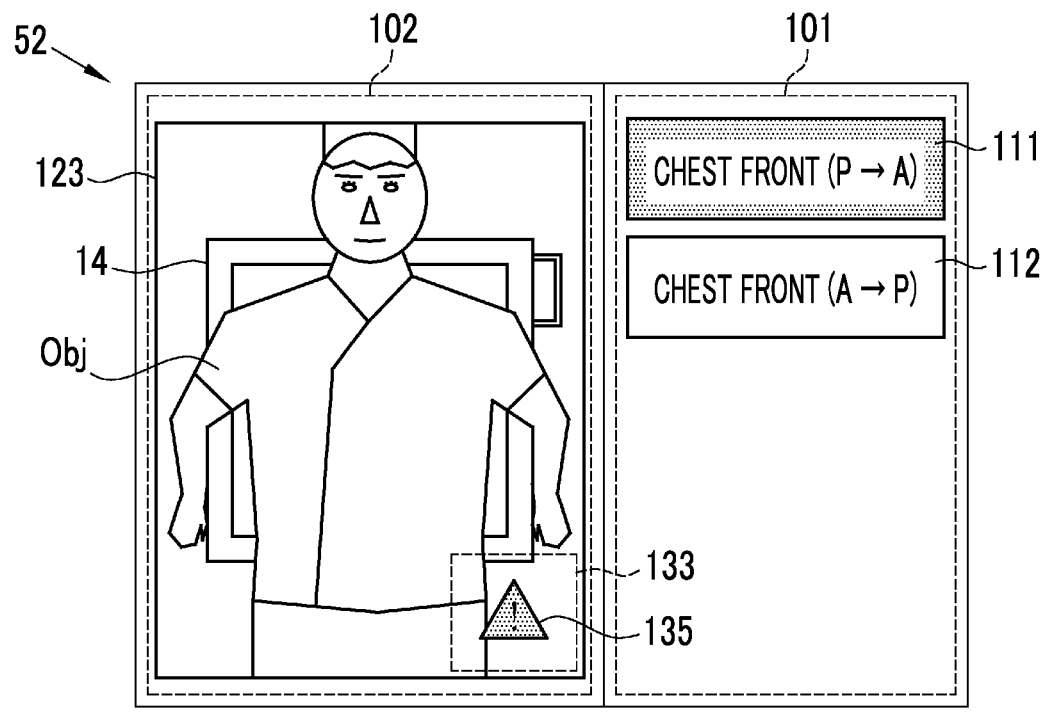
FIG. 8 is an explanatory diagram showing a display aspect of the console in a first display mode.

On the other hand, similarly to the above, even though the first imaging menu 111 having the imaging direction of "P→A" is in the selected state, as shown in FIG. 8, in a camera image 123, there is a case where the abdomen of the subject Obj faces the radiation source 13 and the camera 20 and the back of the subject Obj faces the radiographic unit 14. That is, in the camera image 123, the arrangement of the subject Obj is "A→P". In this case, the recognition unit 54 recognizes that the arrangement of the subject Obj in the camera image 123 does not match the arrangement of the subject Obj in the first imaging menu 111 in the selected state. Therefore, the control unit 56 provides a recognition result display area 133 that is superimposed on, for example, the camera image 123 on the display 52 of the console 30. Then, in the recognition result display area 133, the presence of the recognition result by the recognition unit 54 is displayed by using, for example, a color, a shape, a pattern, or a change (movement) thereof, or a mark 135 or the like (including, in addition to the mark 135, an icon that functions as a GUI, an assistant character formed by imitating a radiological technician or the like, or other forms of notification) indicated by using other visual forms. This is the display of the first display mode on the display 52 of the console 30.

Figure 9:
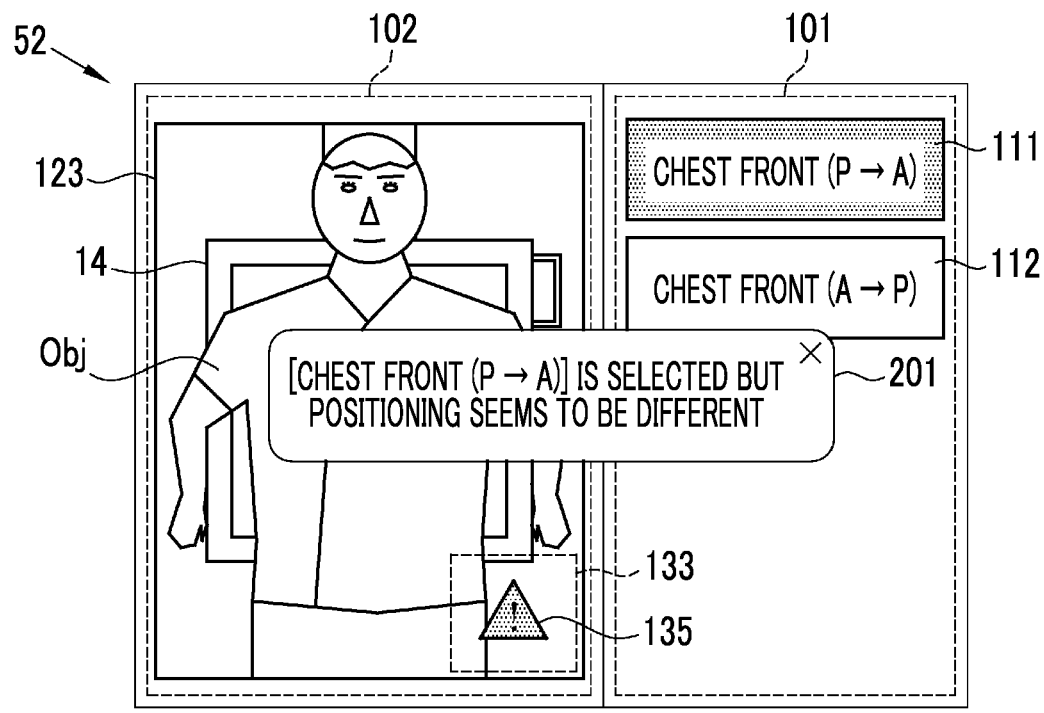
FIG. 9 is an explanatory diagram showing a display aspect of the console in a second display mode.

In the present embodiment, for example, the mark 135 or the like is constituted by a clickable GUI. The control unit 56 receives the click of the mark 135 or the like as an explicit display request for the recognition result. Therefore, as shown in FIG. 9, in a case where the mark 135 or the like is clicked on the console 30, the display 52 of the console 30 displays the specific content of the recognition result in a form of a warning 201 such as "[chest front (P→A)] is selected but positioning seems to be different". This is the display of the second display mode on the display 52 of the console 30. The term "warning" means notification having the content that directly informs a user of the erroneous arrangement of the subject Obj and requests correction of the problem, either directly or indirectly.

<Display of Radiation Source>

Figure 10:
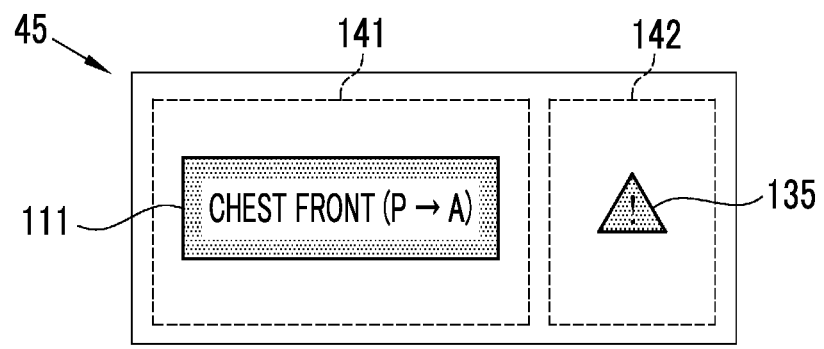
FIG. 10 is an explanatory diagram showing a display aspect of a first display mode on a display of the radiation source.

The display 45 of the radiation source 13 usually has a different display area from the display 52 of the console 30. Therefore, even in a case where the common contents are displayed, the display form of the recognition result and the like on the display 45 of the radiation source 13 is different from the display form on the display 52 of the console 30. For example, as shown in FIG. 10, the display 45 of the radiation source 13 has an imaging menu display area 141 and a recognition result display area 142, at least before the execution of radiography. The imaging menu display area 141 displays the imaging menu in the selected state. This is so that the selected imaging menu can be confirmed in the vicinity of the radiation source 13 (in a range in which the display 45 of the radiation source 13 can be visually recognized). In FIG. 10, the imaging menu in the selected state is the first imaging menu 111. In addition, the recognition result display area 142 displays the presence of the recognition result by the recognition unit 54 by using the mark 135 or the like. This is the display of the first display mode on the display 45 of the radiation source 13.

In a case where there is no selected imaging menu, or in a case where the imaging menu is not set, the imaging menu display area 141 displays that effect. In addition, in a case where there is no selected imaging menu, or in a case where the imaging menu is not set, the imaging menu display area 141 does not display anything, thereby displaying that there is no selected imaging menu or that the imaging menu is not set (selected). In the present embodiment, in a case where the recognition result is a recognition result in which the arrangement of the subject Obj in the camera image matches the arrangement of the subject Obj in the selected imaging menu, nothing is displayed in the recognition result display area 142. Thus, the recognition result display area 142 improves attention drawing performance (easiness of drawing attention of a radiological technician or the like) of the mark 135 or the like as compared with a case where some kind of display is performed intermittently or continuously. In addition, the mark 135 or the like displayed in the recognition result display area 142 may be identical to or different from the mark 135 or the like displayed in the recognition result display area 133 of the console 30. In a case of displaying the mark 135 or the like identical to or similar to that in the recognition result display area 133 or the like of the console 30, the radiological technician or the like can easily know the meaning content and/or importance of the mark 135 or the like displayed in the recognition result display area 142 due to the identity or similarity of the display form. On the other hand, in a case where the mark 135 or the like different from that in the recognition result display area 133 of the console 30 is displayed in the recognition result display area 142, the meaning content and/or importance of the mark 135 or the like may be displayed in an easy-to-understand manner according to the display area or the like.

Figure 11:
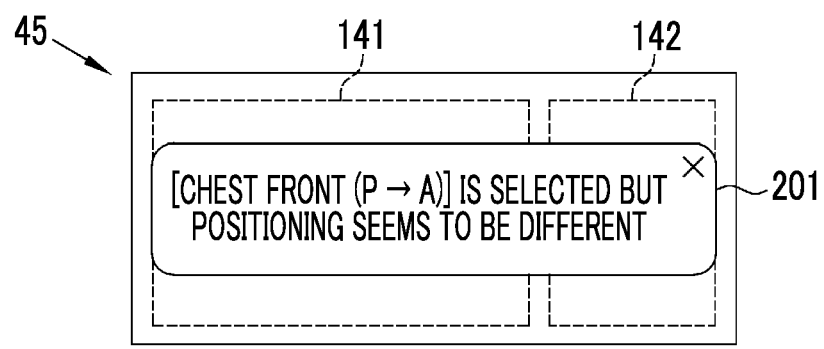
FIG. 11 is an explanatory diagram showing a display aspect of a second display mode on a display of the radiation source.

In the present embodiment, the mark 135 or the like is also constituted by a clickable GUI on the display 45 of the radiation source 13. Therefore, the control unit 56 receives the click of the mark 135 or the like as an explicit display request for the recognition result. As shown in FIG. 11, in a case where the mark 135 or the like is clicked on the radiation source 13, the display 45 of the radiation source 13 displays the specific content of the recognition result in a form of, for example, the warning 201. This is the display of the second display mode on the display 45 of the radiation source 13.

<Display of Tablet Terminal>

The display 61 of the tablet terminal 31 usually has a different display area from the display 52 of the console 30 and/or the display 45 of the radiation source 13. Therefore, even in a case where the contents common to the display 52 of the console 30 and/or the display 45 of the radiation source 13 are displayed, the display form of the recognition result and the like on the display 61 of the tablet terminal 31 is different from the display form on the display 52 of the console 30 and/or the display 45 of the radiation source 13.

Figure 12:
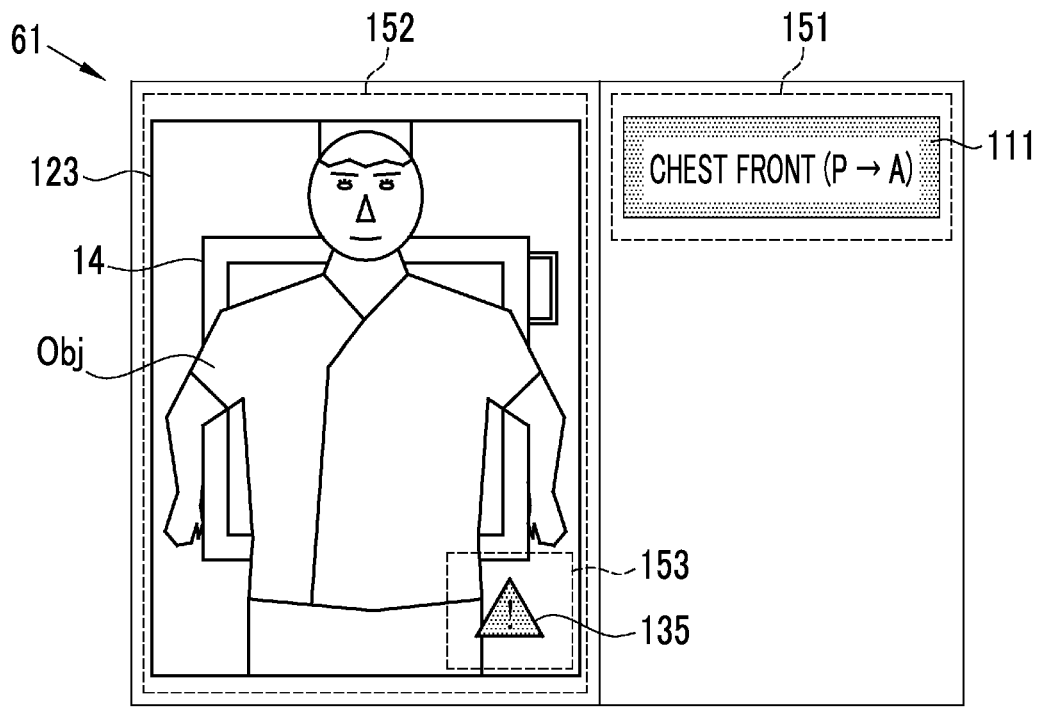
FIG. 12 is an explanatory diagram showing a display aspect of the tablet terminal in the first display mode.

For example, as shown in FIG. 12, the display 61 of the tablet terminal 31 has an imaging menu display area 151 and an image display area 152, at least before the execution of radiography. The imaging menu display area 151 displays the imaging menu in the selected state. This is so that the tablet terminal 31 can be used to confirm the imaging menu selected at any place. In FIG. 12, the imaging menu in the selected state is the first imaging menu 111.

The image display area 152 displays a camera image. In addition, in a case where the recognition result of the recognition unit 54 is a recognition result in which the arrangement of the subject Obj in the camera image does not match the arrangement of the subject Obj in the selected imaging menu, the control unit 56 provides a recognition result display area 153 that is superimposed on the image display area 152. Then, the recognition result display area 153 displays the presence of a matter to be notified about the recognition result by the recognition unit 54 by using the mark 135 or the like. In FIG. 12, the arrangement ("A→P") of the subject Obj in the camera image 123 does not match the arrangement ("P→A") of the subject Obj in the first imaging menu 111 in the selected state. Therefore, the recognition result display area 153 displays the mark 135, thereby displaying the presence of the recognition result by the recognition unit 54. This is the display of the first display mode on the display 61 of the tablet terminal 31. The image display area 152 can display the captured radiation image after the execution of radiography.

Figure 13:
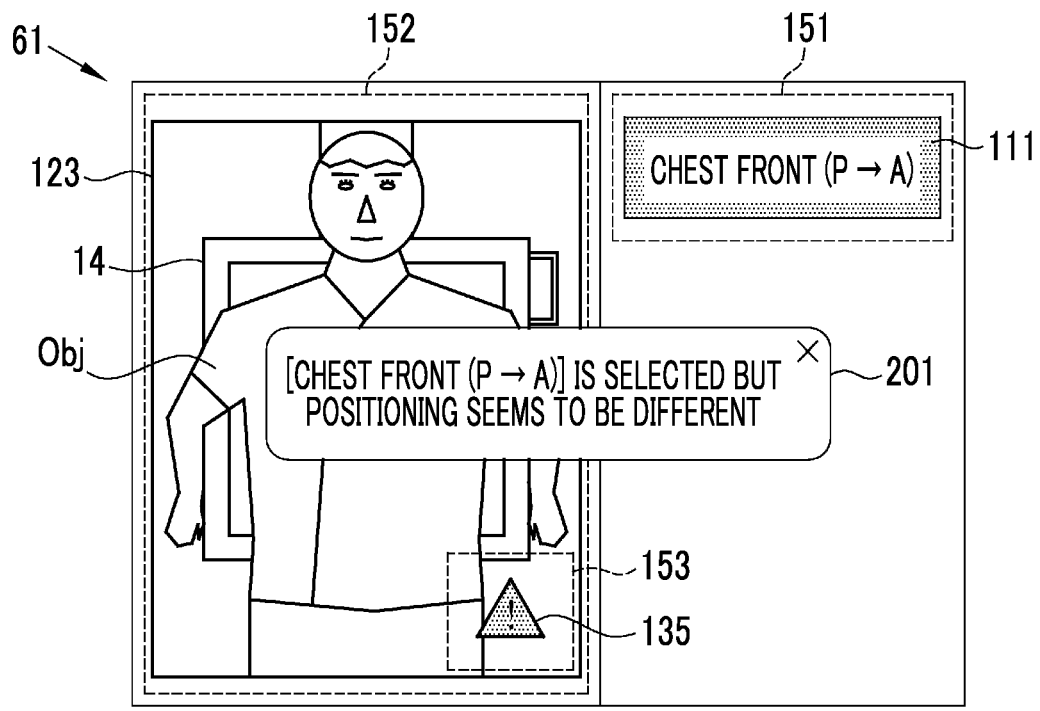
FIG. 13 is an explanatory diagram showing a display aspect of the tablet terminal in the second display mode.

In the present embodiment, for example, the mark 135 or the like is also constituted by a clickable GUI on the display 61 of the tablet terminal 31. Therefore, the control unit 56 receives the click of the mark 135 or the like as an explicit display request for the recognition result. As shown in FIG. 13, in a case where the mark 135 or the like is clicked on the tablet terminal 31, the display 61 of the tablet terminal 31 displays the specific content of the recognition result in a form of, for example, the warning 201. This is the display of the second display mode on the display 61 of the tablet terminal 31.

As described above, the radiographic system 10 displays the specific content of the recognition result in a case where there is an explicit request, through the display of the mark 135 or the like in which the specific content of the recognition result is omitted. Therefore, the radiographic system 10 can support the execution of radiography in accordance with the imaging menu by using the recognition result of the recognition unit 54, and can prevent the radiological technician or the like from excessively relying on the recognition result of the recognition unit 54. This is because the radiographic system 10 displays the specific content of the recognition result only in a necessary case as a result of the determination of the radiological technician or the like, and therefore the radiological technician or the like has to examine the correctness of the arrangement of the subject Obj by himself or herself before receiving the presentation of the content of the recognition result.

The radiographic system 10 displays the presence of the recognition result by the recognition unit 54 and the specific content of the recognition result (hereinafter, referred to as the recognition result and the like) not only on the display 52 of the console 30 but also on the display 45 of the radiation source 13 and the display 61 of the tablet terminal 31. Therefore, in a case where the radiographic system 10 is used, by viewing the display of the recognition result and the like on the display 45 of the radiation source 13 or the display 61 of the tablet terminal 31, the radiological technician or the like can know a possibility of a mistake in the arrangement of the subject Obj on the spot where the subject Obj is arranged without returning to the place where the console 30 is located. As a result, a mistake in the arrangement of the subject Obj can be prevented, and radiography can be smoothly executed.

The radiographic system 10 displays the recognition result and the like, and comprises the plurality of displays separate from the console 30. Therefore, even though the radiological technician or the like moves in order to arrange the subject Obj, there are many opportunities for the radiological technician or the like to quickly and easily know the recognition result or the like at the place after the movement. Therefore, the radiographic system 10 can almost surely prevent a mistake in the arrangement of the subject Obj and can smoothly execute radiography.

In addition, the radiographic system 10 displays the recognition result and the like, and the plurality of displays separate from the console 30 have the different display aspects of the recognition result, respectively. Specifically, the display 45 of the radiation source 13 displays the mark 135 or the like without displaying the camera image, and the display 61 of the tablet terminal 31 displays the mark 135 or the like after displaying the camera image. Therefore, it is possible to appropriately and effectively provide notification about a possibility of a mistake in the arrangement of the subject Obj in accordance with the display area of each display.

In addition, the radiographic system 10 recognizes whether or not the orientation of the subject Obj in the camera image matches the orientation of the subject Obj in the imaging menu, and does not provide the radiation image to the diagnosis in a case where the orientation of the subject Obj in the camera image does not match the orientation of the subject Obj in the imaging menu. Therefore, it is possible to prevent the misidentification of the position of the organ or the disease in the subject Obj, such as the misidentification of situs inversus and/or the misidentification of the left and right disease positions. In particular, in the above embodiment, the recognition unit 54 recognizes the orientation of the subject Obj whose back faces the radiation source 13 and the orientation of the subject Obj whose abdomen faces the radiation source 13. Therefore, it is possible to prevent the misidentification relating to left-right reversal of the subject Obj that is difficult to notice in a case of viewing a large number of radiation images in, for example, a medical examination.

In the above embodiment, the recognition unit 54 recognizes whether or not the orientation of the subject Obj in the camera image matches the orientation of the subject Obj in the imaging menu, but the recognition unit 54 can recognize whether or not the imaging part of the subject Obj recognized by using the camera image matches the imaging part of the subject Obj in the imaging menu, in addition to the recognition of the orientation of the subject Obj or in place of the recognition of the orientation of the subject Obj. In a case where the imaging part of the subject Obj recognized by using the camera image does not match the imaging part in the imaging menu, the control unit 56 displays a warning on the display 45 of the radiation source 13 or the like at that stage, and can provide notification about a possibility of a mistake in the arrangement of the subject Obj. As a result, erroneous imaging of an unnecessary imaging part that does not match the imaging menu can be prevented, and necessary radiography that matches the imaging menu can be smoothly executed.

In the above embodiment, in addition to the display 45 of the radiation source 13 and the display 61 of the tablet terminal 31, the display 52 of the console 30 displays the recognition result and the like, but in a case where the recognition result and the like are displayed on the display 45 of the radiation source 13 or the display 61 of the tablet terminal 31, the display of the recognition result and the like on the display 52 of the console 30 may be omitted. This is because the radiological technician or the like can adjust the arrangement of the subject Obj by viewing the display 45 of the radiation source 13 or the display 61 of the tablet terminal 31 without returning to the console 30. On the contrary, in a case where the recognition result and the like are displayed on the display 52 of the console 30, even though the display 45 of the radiation source 13 or the display 61 of the tablet terminal 31 is provided, the display of the recognition result and the like on the display 45 of the radiation source 13 and/or the display 61 of the tablet terminal 31 can be omitted. This is because, in principle, the radiological technician or the like controls radiography using the console 30.

In the above embodiment, while the warning 201 indicating the specific content of the recognition result is displayed in the second display mode, the radiographic system 10 can display arrangement support information for supporting the arrangement of the subject Obj in the camera image to match the arrangement of the subject Obj in the imaging menu, in addition to the display of the warning 201 indicating the specific content of the recognition result, or in place of the display of the warning 201 indicating the specific content of the recognition result. The arrangement support information is information indicating the orientation or distance of the subject Obj, the radiation source 13, or the radiographic unit 14 that relatively moves or rotates, or the posture (joint bending degree or the like) of the subject Obj. Specifically, a message such as "please turn the abdomen of the subject Obj toward the radiation source 13" is given.

The radiographic system 10 can display the warning 201 and the arrangement support information without displaying the mark 135 or the like. In a case where there is no excessive reliance on the recognition result, the radiological technician or the like can more easily and quickly know the content of the warning 201 by directly displaying the warning 201 and/or the arrangement support information without the display of the mark 135 or the like, and as a result, the radiological technician or the like can smoothly and accurately execute radiography.

In the above embodiment, while the radiographic system 10 displays the content of the recognition result in a case of receiving an explicit display request for the recognition result, the radiographic system 10 can display the second display mode for displaying the content of the recognition result in a case where a certain time (for example, several seconds to several tens seconds) determined by settings or the like has elapsed, in place of an explicit display request for the recognition result. In this case as well, as in the case of receiving an explicit display request for the recognition result, the radiological technician or the like has to examine the correctness of the arrangement of the subject Obj by himself or herself before displaying the specific content of the recognition result. Therefore, while the radiographic system 10 of the present modification example can support the execution of radiography in accordance with the imaging menu by using the recognition result of the recognition unit 54, it can prevent the radiological technician or the like from excessively relying on the recognition result of the recognition unit 54. As described above, in the configuration of displaying the second display mode for displaying the content of the recognition result by the elapse of time, in a case where there is an explicit display request for the recognition result before the display of the content of the recognition result (before the elapse of a predetermined time), the display of the second display mode for displaying the content of the recognition result may be performed based on the explicit display request for the recognition result without waiting for the elapse of time.

In the above embodiment, in a case where a display request for the recognition result is input using the operation unit 46 of the radiation source 13, the content of the recognition result is displayed on the display 45 of the radiation source 13, and in a case where a display request for the recognition result is input using the operation unit 53 of the console 30, the content of the recognition result is displayed using the display 52 of the console 30. Similarly, in a case where a display request for the recognition result is input using the operation unit 62 of the tablet terminal 31, the content of the recognition result is displayed on the display 61 of the tablet terminal 31. However, in a case where a display request for the recognition result is input using the operation unit of any one of the radiation source 13, the console 30, or the tablet terminal 31, the radiographic system 10 can display the content of the recognition result on the corresponding display and/or other display. For example, in a case where a display request for the recognition result is input using the operation unit 53 of the console 30, the content of the recognition result can be displayed not only on the display 52 of the console 30 but also on the display 45 of the radiation source 13 and/or the display 61 of the tablet terminal 31. In this case, even though the radiological technician or the like inputs a display request for the recognition result in the radiation source 13, the console 30, or the tablet terminal 31 and then moves to another place, the content of the recognition result can be quickly confirmed at the movement destination without inputting the display request for the recognition result again. For example, after confirming the content of the recognition result in the console 30, the content of the recognition result can be easily reconfirmed in the radiation source 13. Therefore, the rearrangement of the subject Obj and the radiography can be smoothly executed.

In the above embodiment and modification example, the recognition result and the like are displayed in a case where the arrangement of the subject Obj in the camera image does not match the arrangement of the subject Obj in the imaging menu, but even in a case where the arrangement of the subject Obj in the camera image matches the arrangement of the subject Obj in the imaging menu, the recognition result and the like can be displayed on the display 52 of the console 30, the display 45 of the radiation source 13, and/or the display 61 of the tablet terminal 31. In a case where the arrangement of the subject Obj in the camera image matches the arrangement of the subject Obj in the imaging menu, and in a case where a message or the like indicating that the arrangement of the subject Obj in the camera image matches the arrangement of the subject Obj in the imaging menu or an icon or the like indicating that effect is displayed, the radiological technician or the like can confirm the correctness of the arrangement of the subject Obj by the display. In particular, it is useful in a case where it is difficult to arrange the subject Obj and the radiological technician or the like wants to refer to an objective determination by the recognition unit 54 as to whether or not the subject Obj has been arranged correctly. However, as in the above embodiment, in a case where the recognition result and the like are displayed only in a case where the arrangement of the subject Obj in the camera image does not match the arrangement of the subject Obj in the imaging menu, attention drawing performance in a case where the mark 135 or the like is displayed is improved as compared with a case where some kind of additional display such as the mark 135 is performed intermittently or continuously. Therefore, it is possible to more surely provide notification about the presence of a matter to be notified by the mark 135 or the like.

In the above-described embodiment and modification example, the specific arrangement of the display 45 of the radiation source 13 is optional, but the display 45 of the radiation source 13 is preferably located in a blind spot of the radiographic unit 14. This is because, in a case where the display content of the display 45 of the radiation source 13 can be recognized from the subject Obj arranged in front of the radiographic unit 14, the subject Obj may feel uneasy, and the subject Obj may suffer mental burden in a case where an attention drawing display such as the mark 135 or the warning 201 appears on the display 45. In a case where the display 45 of the radiation source 13 is provided in the blind spot of the radiographic unit 14, the display on the display 45 is difficult to be viewed from the subject Obj due to the arrangement of the subject Obj, the radiation source 13, and the radiographic unit 14. Therefore, it is possible to prevent the subject Obj from feeling uneasy by the display on the display 45.

The blind spot of the radiographic unit 14 refers to an angle range in which the display content on the display 45 of the radiation source 13 is not visible as viewed from the radiographic unit 14. In addition, an angle range in which the display 45 can be visually recognized from the radiographic unit 14 but the display content thereof cannot be substantially recognized is included in the blind spot of the radiographic unit 14. In addition, although the tablet terminal 31 can move to any place, usually, the display content thereof is not intentionally disclosed to the subject Obj. Therefore, the display 61 of the tablet terminal 31 constitutes a display which is substantially in the blind spot of the radiographic unit 14 unless it is arranged in a facility (stand or the like) for disclosing the display content to the subject Obj.

In the above embodiment and modification example, the recognition result and the like are visually notified by displaying the mark 135 or the like on the display 45 of the radiation source 13, but a method of notifying the radiological technician or the like of the recognition result and the like is not limited to visual display. For example, the radiographic system 10 can notify the radiological technician or the like of the recognition result and the like by using sound or voice in a case where there is a speaker, or using vibration or vibration pattern using a motor in a case where there is the motor or the like. Note that, in a case where the recognition result and the like are notified by these methods, it is preferable that the sound or vibration does not give an uneasy feeling to the subject Obj.

In the above embodiment and modification example, the radiographic system 10 can display the progress of the recognition process of the recognition unit 54 on the display 52 of the console 30, the display 45 of the radiation source 13, and the display 61 of the tablet terminal 31. The progress of the recognition process means a state in which the recognition process is performed and the recognition process is not completed, for example, a state in which the recognition unit 54 performs the recognition process, a state in which the recognition process is being performed, a state in which the recognition process is started, and/or a state in which the recognition process is not completed. In this way, in a case of displaying the progress of the recognition process, it is possible to know that the recognition unit 54 is in the recognition process. As a result, it is possible to prevent imaging from being executed while misarranging the subject Obj without waiting for the display of the recognition result and the like.

The radiographic system 10 of the above embodiment and modification example displays the recognition result of the recognition unit 54 on the display 45 of the radiation source 13 at least before the execution of radiography. This is to notify that there is a mistake in the arrangement of the subject Obj or the like before the execution of radiography. In addition, although a timing at which the recognition unit 54 executes the recognition process is optional, it is preferable that the recognition unit 54 recognizes the movement of the subject Obj and executes the recognition process for determining whether or not the arrangement of the subject Obj in the camera image matches the arrangement of the subject Obj in the imaging menu in a case where the movement of the subject Obj stops, and the display 45 of the radiation source 13 displays the result or the like. This is because, usually, in a case where the arrangement of the subject Obj is completed and the radiography is to be executed, the subject Obj is instructed not to move. The "stop" of the movement of the subject Obj includes that the movement of the subject Obj is smaller than, for example, a predetermined reference (threshold value), in addition to a case where the subject Obj is stationary.

In the above embodiment and modification example, there is provided an operation method of the radiographic system including the radiation source 13 that generates the radiation Ra, the radiographic unit 14 that images the subject Obj using the radiation Ra, the camera 20 that images the subject Obj arranged with respect to the radiographic unit 14, and the console 30 that sets the imaging menu, the operation method comprising: a recognition step of recognizing, by the recognition unit 54, whether or not the arrangement of the subject Obj in the camera image captured using the camera 20 matches the arrangement of the subject Obj in the imaging menu; a first display step of displaying, by the displays 45, 52, and 61, the first display mode for indicating the presence of the recognition result; and a second display step of displaying, by the displays 45, 52, and 61, the second display mode for displaying the content of the recognition result in a case where an explicit display request for the recognition result is received.

In the above embodiment and modification example, there is provided a program for driving the radiographic system including the radiation source 13 that generates the radiation Ra, the radiographic unit 14 that images the subject Obj using the radiation Ra, the camera 20 that images the subject Obj arranged with respect to the radiographic unit 14, and the console 30 that sets the imaging menu, the program for executing: a recognition step of recognizing, by using the recognition unit 54, whether or not the arrangement of the subject Obj in the camera image captured using the camera 20 matches the arrangement of the subject Obj in the imaging menu; a first display step of displaying, by using the displays 45, 52, and 61, the first display mode for indicating the presence of the recognition result; and a second display step of displaying the second display mode for displaying the content of the recognition result in a case where an explicit display request for the recognition result is received.

Figure 14:
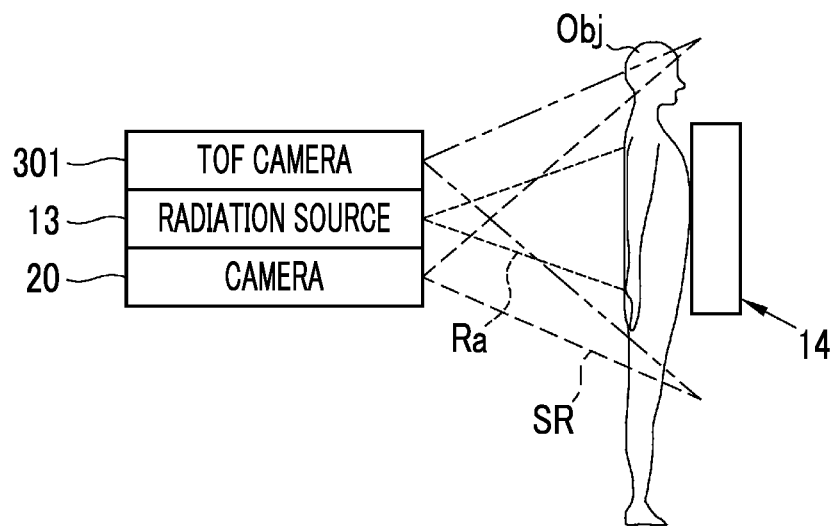
FIG. 14 is an explanatory diagram of a radiographic system of a modification example.

The radiographic system 10 of the above embodiment and modification example may include a configuration for automatically setting the imaging conditions. For example, as shown in FIG. 14, the radiographic system 10 may comprise a time-of-flight (TOF) camera 301 integrally with the radiation source 13. The TOF camera 301 has, for example, a pulse light source that emits pulses. Then, a propagation time of the pulse light is measured by using an image sensor by imaging a range including at least the irradiation range of the radiation Ra using the pulse light emitted from the pulse light source. As a result, the TOF camera 301 measures the distance to the subject Obj. In the present modification example, since the TOF camera 301 is provided integrally with the radiation source 13, the distance to the subject Obj measured by the TOF camera 301 is substantially the distance from the radiation source 13 to the subject Obj (so-called source to object distance (SOD)).

Figure 15:
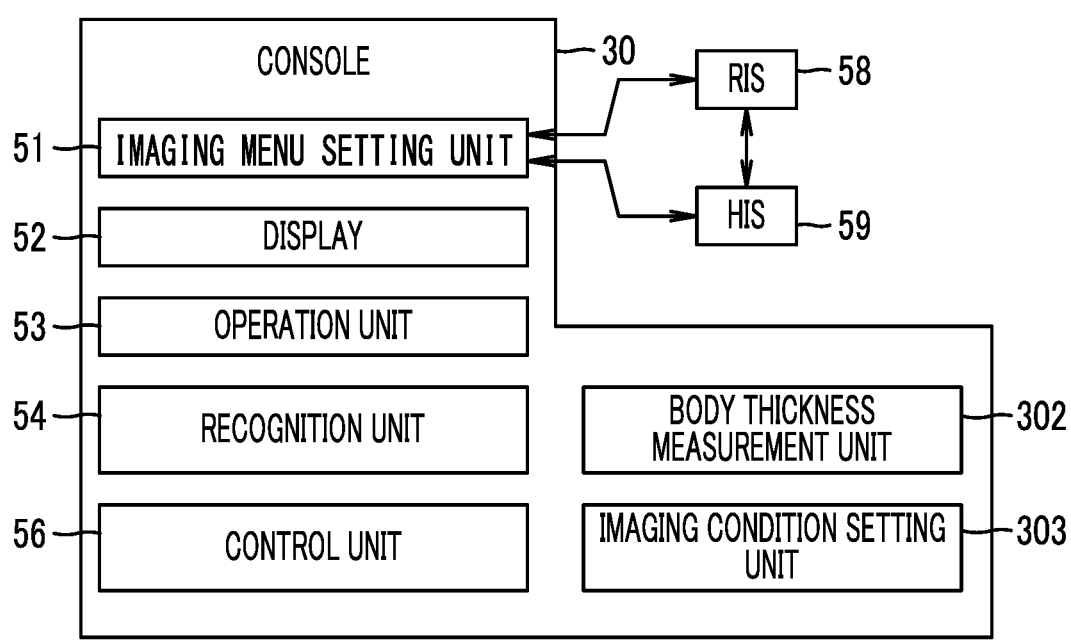
FIG. 15 is a block diagram showing a configuration of a console in the modification example.

As shown in FIG. 15, the console 30 is provided with a body thickness measurement unit 302 and an imaging condition setting unit 303. The body thickness measurement unit 302 measures the body thickness of the subject Obj (in a case where the subject Obj is an object, the body thickness is the thickness of the object) by using a measurement result of the distance to the subject Obj by the TOF camera 301. Specifically, since the source to image distance (SID) is determined by the arrangement of the radiation source 13 and the radiographic unit 14, the body thickness measurement unit 302 can calculate the body thickness of the subject Obj by subtracting the SOD measured using the TOF camera 301, from the SID. In addition, the imaging condition setting unit 303 automatically sets the imaging conditions by using the body thickness of the subject Obj measured by the body thickness measurement unit 302. The imaging conditions are the tube voltage and/or tube current (dose and/or radiation quality of the radiation Ra) of the radiation tube 41, the use or non-use of the grid, the aspect ratio of the grid in a case of being used, and the like.

As described above, in a case where the radiographic system 10 includes a configuration for automatically setting the imaging conditions, the setting of the imaging conditions can be facilitated, whereby radiography can be executed more smoothly.

The TOF camera 301, the body thickness measurement unit 302, and the imaging condition setting unit 303, which are configured to automatically set the imaging conditions, can also be used in a radiographic system which recognizes whether or not the arrangement of the subject Obj in the camera image matches the arrangement of the subject Obj in the imaging menu and does not display the result. In this case, as compared with a radiographic system having no TOF camera 301 or the like, the radiographic system having the configuration for automatically setting the imaging conditions such as the TOF camera 301 facilitates the setting of the imaging conditions, thereby enabling radiography to be executed more smoothly.

In the radiographic system 10 of the above embodiment and modification example, in a case where the camera image (the camera image 103 or the camera image 123 in the above embodiment) is displayed on the display 52 of the console 30 and/or the display 61 of the tablet terminal 31, the display angle of view of the camera image to be displayed can be optionally changed. The display angle of view is a display range of the camera image to be displayed on the display 52 of the console 30 and/or the display 61 of the tablet terminal 31 in the whole captured camera image, and is a part or the whole of the camera image.

Figure 16:
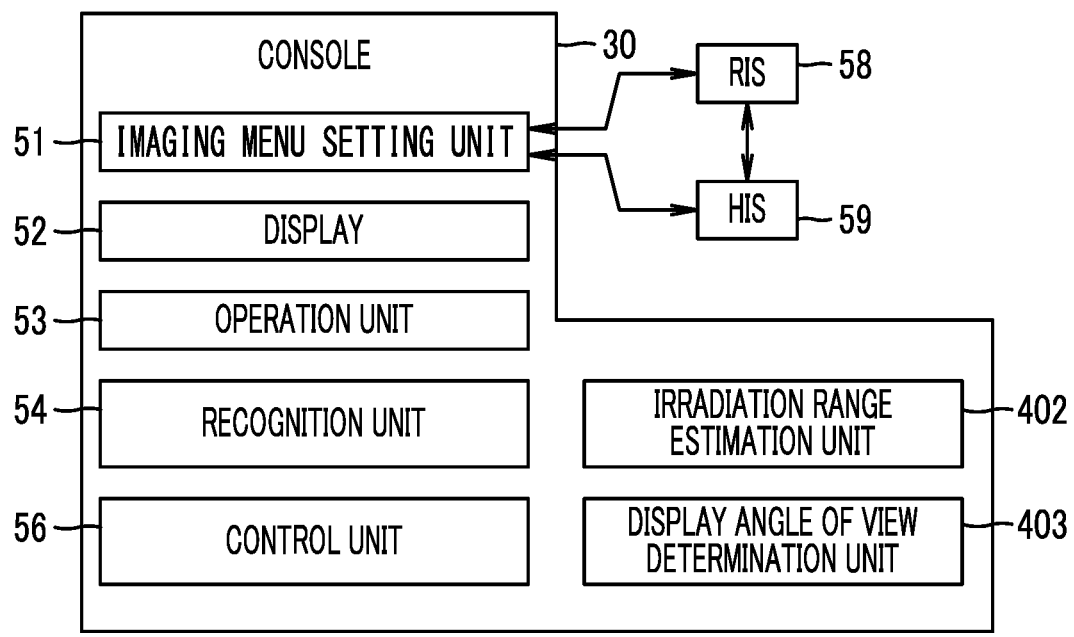
FIG. 16 is a block diagram of a console in a modification example comprising an irradiation range estimation unit and a display angle of view determination unit.

As described above, in a case where the display angle of view of the camera image is variable, as shown in FIG. 16, the radiographic system 10 preferably comprises an irradiation range estimation unit 402 and a display angle of view determination unit 403.

The irradiation range estimation unit 402 estimates the irradiation range of the radiation Ra using the camera image. The irradiation range estimation unit 402 estimates the irradiation range of the radiation Ra by recognizing, for example, the position, size, and/or orientation of the radiographic unit 14 which is captured in the camera image. In addition, in a case where the radiation source 13 has a collimator for adjusting the irradiation range of the radiation Ra, the irradiation range estimation unit 402 acquires information relating to the setting state of the collimator, and can estimate the irradiation range of the radiation Ra using the information. In a case where the irradiation range of the radiation Ra is projected using the irradiation range display unit 43, the irradiation range estimation unit 402 recognizes the display of the irradiation range by the irradiation range display unit 43 in the camera image, and can estimate the irradiation range of the radiation Ra using the result.

The display angle of view determination unit 403 determines the display angle of view of the camera image based on the irradiation range of the radiation Ra estimated by the irradiation range estimation unit 402. The display angle of view determination unit 403 determines the display angle of view such that the irradiation range of the radiation Ra estimated by the irradiation range estimation unit 402 is included, for example, and at least a range smaller than the whole camera image is set as the display range. In addition, the display angle of view determination unit 403 can determine the display angle of view of the camera image such that the display range is equal to the irradiation range of the radiation Ra estimated by the irradiation range estimation unit 402.

In a case where the display angle of view determination unit 403 determines the display angle of view of the camera image, the display 52 of the console 30 and the display 61 of the tablet terminal 31 optimally display a portion of the camera image corresponding to the display angle of view determined by the display angle of view determination unit 403. Specifically, the display 52 of the console 30 makes the center of the irradiation range of the radiation Ra match the center of the image display area 102, and enlarges and displays the portion of the camera image corresponding to the determined display angle of view. Similarly, the display 61 of the tablet terminal 31 makes the center of the irradiation range of the radiation Ra match the center of the image display area 152, and enlarges and displays the portion of the camera image corresponding to the determined display angle of view. Note that, the portion of the camera image corresponding to the display angle of view can be displayed in the original size without being enlarged.

Figure 17:
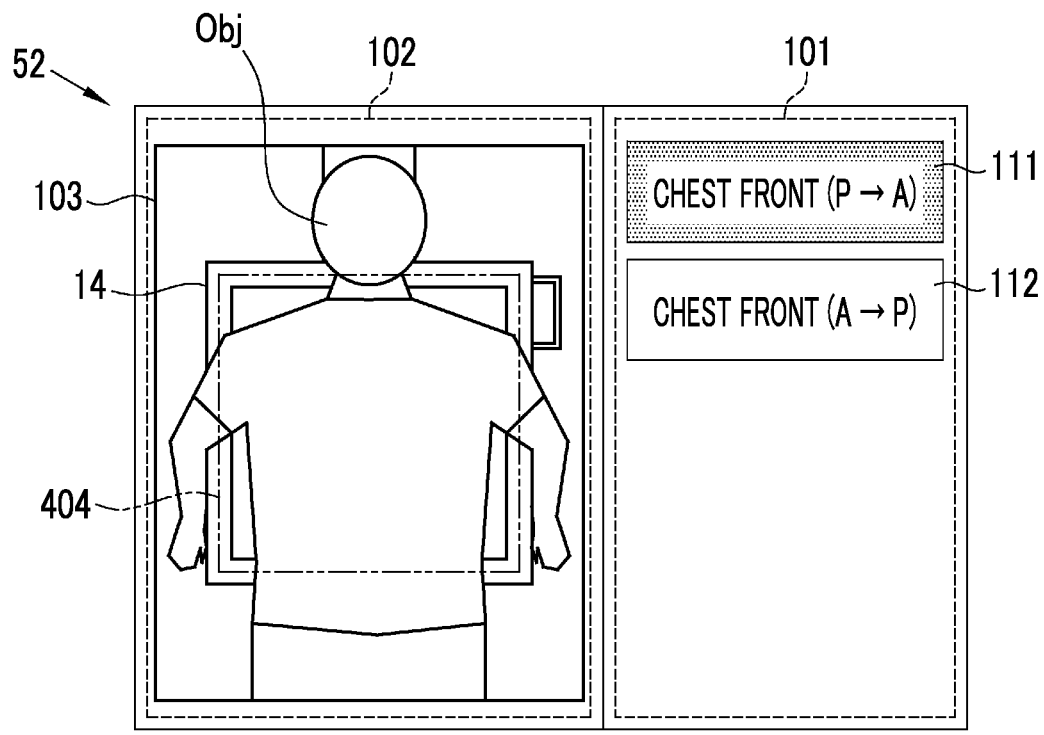
FIG. 17 is an explanatory diagram showing an irradiation range of radiation and a display angle of view.
Figure 18:
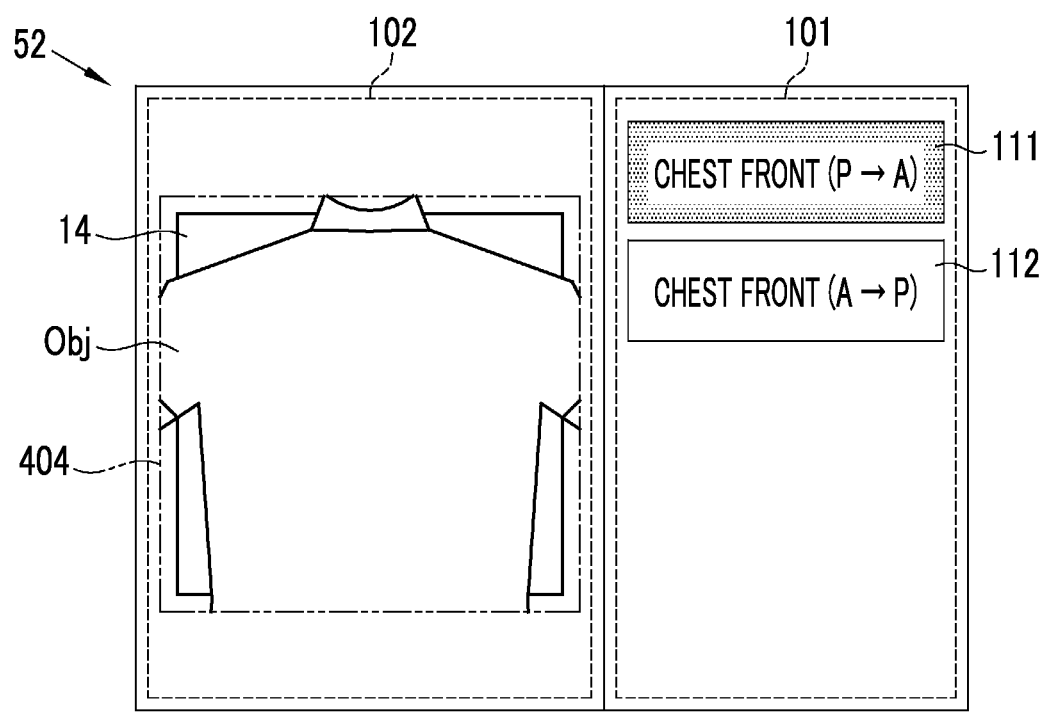
FIG. 18 is an explanatory diagram showing a display aspect after changing the display angle of view.

As described above, the radiographic system 10 comprising the irradiation range estimation unit 402 and the display angle of view determination unit 403 operates as follows, for example. First, before the determination of the display angle of view, the display 52 of the console 30 displays the whole camera image (the whole portion in a case of setting for displaying a part of the camera image) in the image display area 102 (see FIG. 6 or 8). On the other hand, as shown in FIG. 17, in a case where the display angle of view determination unit 403 determines a display angle of view 404 after the irradiation range estimation unit 402 estimates the irradiation range, the display 52 of the console 30 optimally displays a portion corresponding to the determined display angle of view 404 in the image display area 102 by adjusting the position and size. Therefore, according to the radiographic system 10 having the irradiation range estimation unit 402 and the display angle of view determination unit 403, the radiological technician or the like can clearly and surely recognize the irradiation range of the radiation Ra. As a result, it is easy to smoothly and accurately arrange the subject Obj in accordance with the irradiation range of the radiation Ra. The operation of the display 61 of the tablet terminal 31 is the same as the operation of the display 52 of the console 30 described above. In addition, each display form of the first display mode and the second display mode is the same as that of the above embodiment (see FIG. 8 and FIG. 9 and the like).

In the above modification example, although the display angle of view of the camera image is changed, the irradiation range of the radiation Ra may be displayed on the camera image instead of changing the display angle of view of the camera image. In this case, the display angle of view determination unit 403 in the above modification example is omitted or the function thereof is stopped. The display 52 of the console 30 and the display 61 of the tablet terminal 31 display the camera images in the image display area 102 and the image display area 152, respectively, and display, on the camera images, the position, size, and range of the irradiation range of the radiation Ra estimated by the irradiation range estimation unit 402. For example, a frame line indicating the estimated irradiation range of the radiation Ra is superimposed on the camera image. In this way, by emphasizing the estimated irradiation range of the radiation Ra with a frame line or the like, the radiological technician or the like can accurately recognize the irradiation range of the radiation Ra. As a result, it is easy to smoothly and accurately arrange the subject Obj in accordance with the irradiation range of the radiation Ra. In addition, in the display of the display 52 of the console 30 and the display 61 of the tablet terminal 31, it is possible to prevent the irradiation range of the radiation Ra from being chipped.

In the above embodiment and various modification examples, although the display 52 of the console 30 and the display 61 of the tablet terminal 31 each automatically display the camera image, it is preferable that the display and the non-display of the camera image are optionally switched by the radiological technician or the like. However, even in a case where the camera image is not displayed, the recognition unit 54 can recognize the subject Obj and display the first display mode and the second display mode. In addition, even though the camera image is set not to be displayed, the control unit 56 can automatically display the camera image in a case of displaying the first display mode (that is, in a case of displaying the mark 135 or the like). This is so that even in a case where the camera image is not displayed, the arrangement of the subject Obj, which may need to be rearranged, can be easily confirmed without passing through the display setting of the camera image. In addition, in a case where it is necessary to confirm the camera image, it is preferable to display a warning to that effect and prompt the display of the camera image.

In the above embodiment and various modification examples, since the camera 20 is provided substantially integrally with the radiation source 13, in a case where the position of the radiation source 13 (or a portion such as a collimator constituting the radiation source 13) is adjusted or rotated, the orientation of the camera image captured by the camera 20 is also changed. Therefore, it is preferable that the display 52 of the console 30 and the display 61 of the tablet terminal 31 automatically adjust the orientation of the camera image in a case of displaying the camera image. For example, the camera image is rotated and displayed so that the vertical upper part is always positioned above the display 52 of the console 30 and the display 61 of the tablet terminal 31. In addition, the display 52 of the console 30 and the display 61 of the tablet terminal 31 can adjust the overall shape of the camera image in accordance with the image display area 102 and the image display area 152 by trimming the camera image (or adjusting the display angle of view) as needed. In a case where the rectangular camera image is rotated in the image display area 102 and the image display area 152, the camera image is reduced, and therefore the overall shape of the camera image is adjusted as well, so that the subject Obj or the like can be easily confirmed through the camera image.

In the above embodiment and various modification examples, in a case where the first display mode and/or the second display mode is displayed, it is preferable to also display an indicator (it is a so-called certainty degree or reliability degree; hereinafter, referred to as a certainty degree) such as a numerical value indicating the certainty of the recognition result by the recognition unit 54. This is so that the radiological technician or the like can determine the reliability of the recognition result almost intuitively by viewing the display of the certainty degree since the display of the certainty degree can be used an indicator for determining whether or not the recognition result is reliable. The certainty degree can be output together with the recognition result by the recognition unit 54 in association with the recognition process.

In addition, in the above embodiment and modification example, a part or the whole can be used in any combination.

In the above embodiment, the hardware structure of a processing unit executing various processes such as the imaging menu setting unit 51, the operation unit 53, the recognition unit 54, the control unit 56, the body thickness measurement unit 302, the imaging condition setting unit 303, the irradiation range estimation unit 402, and the display angle of view determination unit 403 is any of the following various processors. The various processors include a central processing unit (CPU) that is a general-purpose processor that executes software (programs) to function as various processing units, a graphical processing unit (GPU), a programmable logic device (PLD) that is a processor capable of changing a circuit configuration after manufacture, such as a field programmable gate array (FPGA), and an exclusive electric circuit that is a processor having a circuit configuration exclusively designed to execute various processes.

One processing unit may be constituted by one of these various processors, or may be a combination of two or more processors of the same type or different types (for example, a plurality of FPGAs, a combination of a CPU and an FPGA, or a combination of a CPU and a GPU). In addition, a plurality of processing units may be constituted by one processor. As an example in which the plurality of processing units are constituted by one processor, first, as represented by a computer such as a client or a server, one processor is constituted by a combination of one or more CPUs and software and this processor functions as the plurality of processing units. Second, as represented by a system on chip (SoC) or the like, a processor that realizes the functions of the entire system including the plurality of processing units by using one integrated circuit (IC) chip is used. As described above, the various processing units are constituted by using one or more of the above described various processors as the hardware structure.

Further, the hardware structure of these various processors is more specifically an electric circuit (circuitry) in a form in which circuit elements such as semiconductor elements are combined.

EXPLANATION OF REFERENCES

10: radiographic system
13: radiation source
14: radiographic unit
20: camera
30: console
31: tablet terminal
41: radiation tube
42: high voltage generation circuit
43: irradiation range display unit
45: display
46: operation unit
51: imaging menu setting unit
52: display
53: operation unit
54: recognition unit
56: control unit
58: RIS
59: HIS
61: display
62: operation unit
101: imaging menu display area
102: image display area
103: camera image
111: first imaging menu
112: second imaging menu
113: radiation image
123: camera image
133: recognition result display area
135: mark
141: imaging menu display area
142: recognition result display area
151: imaging menu display area
152: image display area
153: recognition result display area
201: warning
301: TOF camera
302: body thickness measurement unit
303: imaging condition setting unit
402: irradiation range estimation unit
403: display angle of view determination unit
404: display angle of view

What is claimed is:

1. A radiographic system comprising:
a radiation source that generates radiation;
a radiographic unit that images a subject using the radiation;
a camera that images the subject arranged with respect to the radiographic unit;
a processor; and
a display,
wherein the processor
sets an imaging menu,
recognizes whether or not arrangement of the subject in a camera image captured using the camera matches arrangement of the subject in the imaging menu, and
displays a first display mode for indicating presence of a result of the recognition, and displays a second display mode for displaying a content of the recognition result in a case of receiving an explicit display request for the recognition result, on the display.

2. The radiographic system according to claim 1,
wherein the display is located in a blind spot of the radiographic unit.

3. The radiographic system according to claim 1,
wherein the display is provided in the radiation source.

4. The radiographic system according to claim 1,
wherein the display is a tablet terminal.

5. The radiographic system according to claim 1,
wherein a plurality of the displays are provided.

6. The radiographic system according to claim 5,
wherein the plurality of displays have different display aspects of the recognition result, respectively.

7. The radiographic system according to claim 1,
wherein the processor recognizes whether or not an orientation of the subject in the camera image matches an orientation of the subject in the imaging menu.

8. The radiographic system according to claim 7,
wherein the processor recognizes an orientation of the subject whose back faces the radiation source and an orientation of the subject whose abdomen faces the radiation source.

9. The radiographic system according to claim 1,
wherein the processor recognizes whether or not an imaging part of the subject recognized by using the camera image matches an imaging part of the subject in the imaging menu.

10. The radiographic system according to claim 1,
wherein the processor displays, on the display, a warning indicating that the arrangement of the subject in the camera image does not match the arrangement of the subject in the imaging menu.

11. The radiographic system according to claim 1,
wherein the processor displays, on the display, arrangement support information for supporting the arrangement of the subject in the camera image to match the arrangement of the subject in the imaging menu.

12. The radiographic system according to claim 1,
wherein the processor prohibits irradiation with the radiation in a case where the arrangement of the subject in the camera image does not match the arrangement of the subject in the imaging menu.

* * * * *